United States Patent [19]

McKibben et al.

[11] 4,027,420
[45] June 7, 1977

[54] AIR DROPPED BAIT DISPENSERS FOR ATTRACTING AND KILLING THE COTTON BOLL WEEVIL

[75] Inventors: Gerald H. McKibben; Theodore B. Davich, both of Starkville, Miss.

[73] Assignee: The United States of America as represented by the Secretary of Agriculture, Washington, D.C.

[22] Filed: Sept. 19, 1975

[21] Appl. No.: 615,035

[52] U.S. Cl. .................................... 43/124; 43/131
[51] Int. Cl.² ........................................ A01M 1/20
[58] Field of Search .......................... 43/114–117, 43/124,131; 244/136, 138; 424/17, 84, 219

[56] References Cited

UNITED STATES PATENTS

| 944,882 | 12/1909 | Laube et al | 43/114 |
| 3,304,646 | 2/1967 | Staley | 43/114 |
| 3,729,858 | 5/1973 | Bradshaw | 43/114 |
| 3,755,962 | 9/1973 | Walters et al. | 244/136 |
| 3,863,384 | 2/1975 | Weatherston et al. | 43/114 |
| 3,882,227 | 5/1975 | Bradburne | 424/219 |
| 3,937,826 | 2/1976 | Harris | 424/17 |

FOREIGN PATENTS OR APPLICATIONS

| 1,477,867 | 3/1967 | France | 43/113 |

*Primary Examiner*—Russell R. Kinsey
*Assistant Examiner*—Peter K. Skiff
*Attorney, Agent, or Firm*—M. Howard Silverstein; David G. McConnell

[57] ABSTRACT

A new apparatus and method for attracting and killing cotton boll weevils is disclosed. Specifically this apparatus consists of a toxic material affixed to a substrate which is air dropped onto fields of growing cotton. Boll weevils are attracted to these air dropped baited traps and killed upon contact.

7 Claims, 2 Drawing Figures

AIR DROPPED BAIT DISPENSERS FOR ATTRACTING AND KILLING THE COTTON BOLL WEEVIL

This invention relates to an apparatus and method for killing or destroying cotton boll weevils. More specifically, this invention relates to a unique method and means of air dropping baited dispensers onto a field of cotton, said dispensers subsequently killing or destroying the boll weevils as a result of the boll weevils feeding upon the baited traps.

In the prior art the literature teaches that for several years grandlure baited traps have been used across the cotton belt with considerable success for survey and for migration studies of the boll weevil. Tests have also been conducted to investigate their usefulness in suppression and control. The earliest traps used were coated with a sticky material to capture the weevils that responded to it. There were, subsequently, traps made of plastic or paper in the form of a container attached to the top of a cone to capture the weevils alive. However, the need developed for a low-cost device to attract and kill boll weevils. The devices described herein serve to fill this need.

The devices described herein consist of two parts connected by a string, to give aerodynamic balance, so that when dropped or tossed into a field or other plant foliage said devices will hang up in the foliage. Traps in foliage have been found to be more effective in capturing boll weevils than those placed on the ground.

The instant invention can take on the form of a square, triangle circle, tube, sphere, etc., and can be constructed of paper, plastic, etc., and connected by a string or wire so as to provide proper effective orientation when dropped into cotton plants or other plant foliage.

The main objective of this invention is to design and build a trap to kill or destroy boll weevils.

It is another object of this invention to build and provide very inexpensive bait dispensers.

A third object of this invention is to provide a trap which can be air dropped.

A fourth object of this invention is to provide a means of sterilizing boll weevils.

A fifth object of this invention is to improve cotton production by the elimination of boll weevils.

Other objects and advantages for this invention will further become apparent hereinafter and in the drawings, in which.

Figure 1:
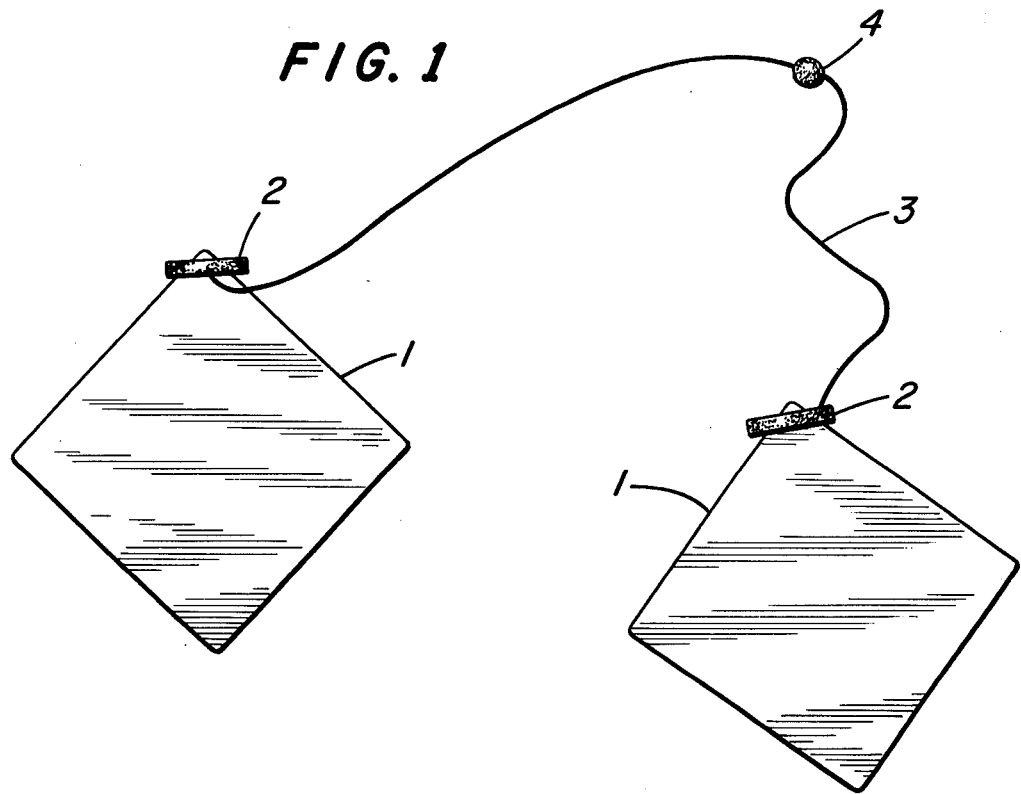
FIG. 1 is a top view of one embodiment of the invention using a square poster board as a matrix for the toxicant.
Figure 2:
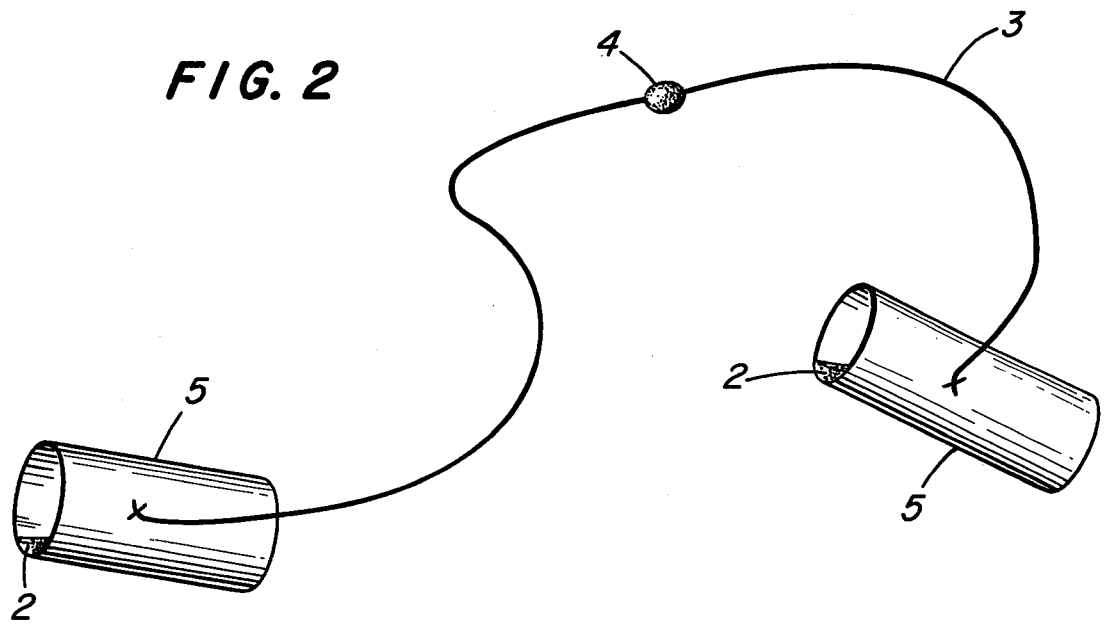
FIG. 2 is a schematic view of one embodiment of the invention using a cylindrical cardboard tube as a matrix for the toxicant.

In describing the preferred embodiment of the invention illustrated in the drawings, specific terminology will be resorted to for the sake of clarity. However, it is not intended to be limited to the specific terms so selected, and it is to be understood that each specific term includes all technical equivalents which operate in a similar manner to accomplish a similar purpose.

Turning now to the specific embodiment of the invention selected for illustration in FIG. 1, the number 1 designates a poster board square forming a base member. Two of these squares are ties together using wire or string 3. Square size is not critical but 7 inches was used for the instant invention. The tie distance should be sufficient to allow for the squares to efficiently catch and hang on a cotton plant and give good aerodynamic balance when dropped into a cotton field from a plane. A twelve-inch length of string was used for the instant invention. In one corner of each square is fastened a reservoir 2 to contain a bait solution. The bait solution can be any toxicant or sterilant effective against boll weevils. For the instant invention the following toxicant was used:

| | % by weight |
|---|---|
| Invert sugar | 50.00 |
| Water extract of cotton flowers | 44.55 |
| Fumaric acid | .15 |
| Sodium benzoate | .10 |
| Glycerol | 5.00 |
| O,O-Dimethyl-2, 2-dichlorovinyl phosphate (DDVP) | 0.20 |

Any material which will readily absorb and hold the toxicant can be used to construct the reservoir. In the case of the instant invention cigarette filters and 1-inch cotton dental roll were found to be effective.

On the string is fastened a pellet containing grandlure which acts to attract the weevils. In the instant embodiment grandlure (composed of pheremone) in a polyethylene glycol-impregnated filter was used. The cards were painted yellow to improve their attracting ability to the weevils.

The second embodiment of the instant invention, as shown in FIG. 2, is the same as that described above for FIG. 1 except cardboard cylinders 5 were used instead of 7 inch squares 1, and the bait reservoir 2 is placed inside the cylinder.

In the case of both embodiments described in FIGS. 1 and 2, a number of such devices are air dropped into a cotton field where they land in the foliage and are thus displayed in a position to attract and destroy or kill boll weevils.

The two parts connected by the string are biodegradable and can consist of squares, tubes, or other shapes, and combinations thereof, constructed of paper, cardboard, plastic, or other materials.

The reservoir may contain bait as toxicant, chemosterilant, control agents such as pathogens, growth regulating hormones, or dyes used to mark boll weevils.

Having thus described my invention, I claim:

1. An apparatus capable of being dropped from an airplane used to attract and kill boll weevils comprising in combination
   a. two base members;
   b. means for connecting together said base members such that the maximum distance between said base members is sufficient to give the apparatus aerodynamic balance when said apparatus is dropped from an airplane;
   c. a grandlure mixture serving as an attractant affixed to said means;
   d. a bait means affixed to each base member, said bait means impregnated with a toxic material.

2. The apparatus as defined in claim 1 wherein the aparatus is bio-degradable and the toxic material is:

| | % by weight |
|---|---|
| Invert sugar | 50.00 |
| Water extract of cotton flowers | 44.55 |
| Fumaric acid | .15 |
| Sodium Benzoate | .10 |

-continued

| | % by weight |
|---|---|
| Glycerol | 5.00 |
| O,O-Dimethyl-2,2-dichlorovinyl phosphate (DDVP) | .20 |

3. A method for attracting, killing, or destroying boll weevils comprising in combination:
 a. tying two base members which are painted yellow and sprayed with a toxic material together using
 b. a tie means which is affixed to
 c. a grandlure, mixture serving as an attractant
 d. and a bait means affixed to each base member said bait means
 e. impregnated with
 f. a material which is toxic to boll weevils, and
 g. thereafter air dropping the said combination onto a cotton field where said combination attracts and kills or destroys boll weevils.

4. An apparatus capable of being dropped from an airplane used to attract and kill boll weevils comprising in combination:
 a. two base members;
 b. means for connecting together said base members such that the maximum distance between said base members is sufficient to give the apparatus aerodynamic balance when said apparatus is dropped from an airplane;
 c. a grandlure mixture serving as an attractant affixed to said means;
 d. a bait means affixed to each base member, said bait means impregnated with a pathogen.

5. An apparatus capable of being dropped from an airplane used to attract and kill boll weevils comprising in combination:
 a. two base members;
 b. means for connecting together said base members such that the maximum distance between said base members is sufficient to give the apparatus aerodynamic balance when said apparatus is dropped from an airplane;
 c. a grandlure mixture serving as an attractant affixed to said means;
 d. a bait means affixed to each base member, said bait means impregnated with a growth regulating hormone.

6. An apparatus capable of being dropped from an airplane used to attract and sterilize boll weevils comprising in combination:
 a. two base members;
 b. means for connecting together said base members such that the maximum distance between said base members is sufficient to give the apparatus aerodynamic balance when said apparatus is dropped from an airplane;
 c. a grandlure mixture serving as an attractant affixed to said means;
 d. a bait means affixed to each base member, said bait means impregnated with a chemosterilant.

7. An apparatus capable of being dropped from an airplane used to attract and mark boll weevils comprising in combination:
 a. two base members;
 b. means for connecting together said base members such that the maximum distance between said base members is sufficient to give the apparatus aerodynamic balance when said apparatus is dropped from an airplane;
 c. a grandlure mixture serving as an attractant affixed to said means;
 d. a bait means affixed to each base member, said bait means impregnated with a dye.

* * * * *